(12) United States Patent
Chen et al.

(10) Patent No.: US 10,139,365 B2
(45) Date of Patent: Nov. 27, 2018

(54) METAL OXIDE PH SENSOR

(71) Applicant: COMMONWEALTH SCIENTIFIC AND INDUSTRIAL RESEARCH ORGANISATION, Canberra ACT (AU)

(72) Inventors: Miao Chen, Mount Waverley (AU); Mikko Vepsalainen, Elwood (AU)

(73) Assignee: COMMONWEALTH SCIENTIFIC AND INDUSTRIAL RESEARCH ORGANISATION, Acton ACT (AU)

( * ) Notice: Subject to any disclaimer, the term of this patent is extended or adjusted under 35 U.S.C. 154(b) by 0 days.

(21) Appl. No.: 15/507,850

(22) PCT Filed: Aug. 28, 2015

(86) PCT No.: PCT/AU2015/000521
§ 371 (c)(1),
(2) Date: Mar. 1, 2017

(87) PCT Pub. No.: WO2016/033632
PCT Pub. Date: Mar. 10, 2016

(65) Prior Publication Data
US 2017/0336351 A1 Nov. 23, 2017

(30) Foreign Application Priority Data
Sep. 1, 2014 (AU) .............................. 2014903484

(51) Int. Cl.
G01N 27/333 (2006.01)
G01N 27/416 (2006.01)
G01N 27/30 (2006.01)

(52) U.S. Cl.
CPC ....... *G01N 27/4167* (2013.01); *G01N 27/302* (2013.01)

(58) Field of Classification Search
CPC . G01N 27/302; G01N 27/333; G01N 27/3335
See application file for complete search history.

(56) References Cited

U.S. PATENT DOCUMENTS 4,935,265 A 6/1990 Pike
5,009,766 A 4/1991 Lauks
(Continued)

FOREIGN PATENT DOCUMENTS

CN 103310994 A 9/2013
EP 0 757 246 A2 2/1997
(Continued)

OTHER PUBLICATIONS

Xu et al., "Modification of vertically aligned carbon nanotubes with RuO2 for a solid-sate pH sensor," Electrochimica Acta 55 (2010) 2859-2864 (Year: 2010).*
(Continued)

*Primary Examiner* — Alexander S Noguerola
(74) *Attorney, Agent, or Firm* — Ladas & Parry LLP

(57) ABSTRACT

A pH sensor comprising a metal oxide-polymer composite, comprising: a continuous polymer resin matrix; and a solid particulate, component dispersed in the polymer resin matrix comprising (i) metal oxides and (ii) a particulate carbon-based conductor wherein the metal oxides comprise $Ta_2O_5$ and $RuO_2$ in a weight ratio of $Ta_2O_5:RuO_2$ (on the basis of weight of metal component) in the range of from 90:10 to 10:90.

18 Claims, 3 Drawing Sheets

(56) References Cited

U.S. PATENT DOCUMENTS

| | | | |
|---|---|---|---|
| 6,860,984 | B2 | 3/2005 | Bannigan et al. |
| 8,486,238 | B2 | 7/2013 | Park et al. |
| 8,552,730 | B2* | 10/2013 | Chiao .................. G01N 27/403 204/409 |
| 8,585,999 | B2 | 11/2013 | Keister |
| 2012/0308468 | A1 | 12/2012 | Choi et al. |
| 2013/0150689 | A1 | 6/2013 | Shaw-Klein |
| 2013/0199944 | A1 | 8/2013 | Petisee |

FOREIGN PATENT DOCUMENTS

| | | |
|---|---|---|
| WO | 2000/04379 | 1/2000 |
| WO | 2012/003223 A1 | 1/2012 |

OTHER PUBLICATIONS

Manjakkal et al., "Fabrication of thick film sensitive $RuO_2$—$TiO_2$ and Ag/AgCl/KCl reference electrodes and their application for pH measurements," Sensors and Actuators B: Chemical 204 (2014) 57-67. Available online Jul. 31, 2014 (Year: 2014).*

MuRata article entitled, "The Structure and Principle of Electrical Double Layer Capacitor" Downloaded on Apr. 19, 2018 from https://www.murata.com/en-us/products/capacitor/edlc/techguide/principle (Year: 2018).*

Article entitled "Tantalum Capacitor" downloaded on Apr. 19, 2018 from http://www.capacitorguide.com/tantalum-capacitor/ (Year: 2018).*

Giancarlo R. Salazar-Banda, et al.; 'The influence of different co-catalysts in PT-based ternary and quaternary electro-catalysts on the electro-oxidation of methanol and ethanol in acid media'; Journal of Electroanalytical Chemistry; 2012; vol. 668; pp. 13-25; pp. 15, section 2; p. 14-15 bridging paragraph; Table 1; p. 15-17, section 3.1; Figures 1 and 3.

CN 103310994 A _ English Translation.

Hongmei Quan, et al.; 'Surface Renewable Hydrogen Ion-Selective Polymeric Composite Electrode Containing Iridium Oxide'; Bull. Korean Chem. Soc.; 2005; vol. 26; No. 10; pp. 1565-1568; Abstract.

Josimar Ribeiro, et al.; 'Morphological and electrochemical investigation of $RuO_2$—$Ta_2O_5$ oxide films prepared by the Pechini-Adams method'; Journal of Applied Electrochemistry; 2008; vol. 38; pp. 767-775; Abstract; p. 768; section 2. 1; table 1.

Jung-Chuan Chou, and Wei-Lun Hsia; Study on the Characteristics of the Measurement System for pH Array Sensors; World Academy of Science, Engineering and Technology; vol. 3; No. 5; May 23, 2009.

M. Brischwein et al.; Planar Ruthenium Oxide Sensors for Cell-on-a-Chip Metabolic Studies; Chem. Anal. (Warsaw), 54, 1193 (2009).

Peter Kurzweil; Metal Oxides and Ion-Exchanging Surfaces as pH Sensors in Liquids: State-of-the-Art and Outlook; Sensors (Basel); 2009; 9(6): 4955-4985; Published online Jun. 23, 2009. doi: 10.3390/s90604955.

Wen-Ding Huang et al.; A flexible pH sensor based on the iridium oxide sensing film; Sensors and Actuators A 169 (2011) 1-11.

G. M. da Silva et al.; Development of low-cost metal oxide pH electrodes based on the polymeric precursor method; Analytica Chimica Acta 616; 2008; 36-41.

Alexsandro M. Zimer et al.; Needle-like IrO/Ag combined pH microelectrode; Electrochemistry Communications 12 (2010) 1703-1705.

Miao Chen et al.; Electrochemical impedance spectroscopy study of $Ta_2O_5$ based EIOS pH sensors in acid environment; Sensors and Actuators B 192 (2014) 399-405.

Ribeiro et al. "Characterization of $RuO_2$—$Ta_2O_5$ Coated Titanium Electrode Microstructure, Morphology, and Electrochemical Investigation", Journal of The Electrochemical Society, 151 (10) D106-D112 (2004).

Koncki et al. "Screen-printed rutheneum dioxide electrodes for pH measurements", Analytica Chemica Acta, vol. 351, No. 1-3, Sep. 1, 1997, 143-149.

English translation of JPH05043063U.

* cited by examiner

Figure 3a                    Figure 3b

METAL OXIDE PH SENSOR

RELATED APPLICATION

This application is a national phase entry under 35 USC 371 of International Patent Application No.: PCT/AU2015/000521 filed on 28 Aug. 2015, which claims priority from Australian Application No. 2014903484 filed on 1 Sep. 2014, the disclosures of which are incorporated in their entirety by reference herein.

FIELD

The invention relates to a pH sensor comprising a metal oxide-polymer composite. The composite comprises metal oxide particles, specifically $Ta_2O_5$ and $RuO_2$, and carbon-based conducting particles dispersed in a polymer matrix.

BACKGROUND pH is one of the most important chemical parameters for monitoring chemical and biological processes. It is commonly used, for example, in the food industry, minerals processing, bioprocessing and environment monitoring. pH is commonly measured by using glass pH electrodes. Glass pH electrodes have good sensitivity and stability. However, they suffer from a number of serious disadvantages, such as high impedance, mechanical fragility, instability in very acidic solutions and high temperatures, slow response and vulnerability to membrane fouling. For applications where the volume of solution is restricted, glass electrodes are not suitable due to the difficulties in miniaturization.

As a result, non-glass pH sensors, especially solid-state pH sensors using metal oxides, began to draw considerable attention, because they are robust and less sensitive to cation interference. Fog et al., Sensors and Actuators, 1984, 5, 137-148) describe metal oxide films formed on the surface of precious metal electrodes and their use in measuring hydrogen ion concentration. Electrode potentials due to the oxidation-reduction reaction of the metal oxides are dependent on the hydrogen ion concentration. The useful metal oxides include $TiO_2$, $RuO_2$, $RhO_2$, $SnO_2$, $Ta_2O_5$, $OsO_2$, $PdO_2$, $PtO_2$, $IrO_2$, and the like. The hydrogen ion selective electrodes using metal oxides are mostly based on the fact that the potentials due to the reversible oxidation-reduction reactions of the metal oxides are dependent on the hydrogen ion concentration. These metal/metal oxide electrodes exhibit a Nernstian or near-Nernstian response to pH. However, there are also several drawback compared to glass pH electrodes. Most significant ones are (i) interference caused by halogen anions, redox active species and complexing agents, (ii) drift and (iii) hysteresis.

Quan et al., Bull, Korean Chem, Soc. 2005, 26, 1585-1588) describes iridium oxide/carbon-polymer composite hydrogen ion electrodes. These composite electrodes are said to have an advantage in that they are composed of polymer materials and carbon black particles or graphite particles, which are conductors, and uniformly include iridium oxide particles, exhibiting selective sensitivity to hydrogen ion. The electrodes have hydrogen ion selectivity and physical stability due to the mechanical strength of the polymers, thereby easily obtaining a renewable electrode surface through a simple polishing process, whenever the electrodes are inactivated or contaminated.

Iridium oxide/carbon-polymer composite pH electrodes have problems in that, although the electrodes have improved physical stability and surface renewability compared to conventional glass electrodes or polymer film electrodes, the manufacturing method of the electrode is complicated, the pH dependency of the electrodes varies greatly depending on the electrodes, and hysteresis occurs during repeated use of the electrodes. U.S. Pat. No. 8,486,238 addresses the problems of the Quan et al. composite electrode by providing an iridium oxide glass or ceramic composite electrode which formed by sintering at a temperature of preferably 600° C. to 800° C. for 3 to 5 hours.

Miao et al., Sensors and Actuators B, 192 (2014)399-405 disclose a tantalum pentoxide based electrolyte-ion sensitive membrane-oxide-semiconductor (EIOS) pH sensor and studies possible interference from a range of metal ions in acid solutions.

The discussion of the background to the invention herein is included to explain the context of the invention. This is not to be taken as an admission that any of the material referred to was published, known or part of the common general knowledge as at the priority date of any of the claims.

SUMMARY

We provide a pH sensor comprising a metal oxide-polymer composite, comprising:
  a continuous polymer resin matrix; and
  a solid particulate component dispersed in the polymer resin matrix comprising (i) metal oxides and (ii) a particulate carbon-based conductor
  wherein the metal oxides comprise $Ta_2O_5$ and $RuO_2$ in a weight ratio of $Ta_2O_5:RuO_2$ (on the basis of weight of metal component) in the range of from 90:10 to 10:90, preferably from 80:20 to 20:80 and more preferably from 70:30 to 30:70.

In one embodiment the metal oxide-polymer composite comprises:
  a polymer matrix in an amount of y weight of the composite composition and dispersed in the matrix a mixture of particulate materials comprising:
  particulate $Ta_2O_5$ in an amount of at least 5% by weight (determined as Ta) of the composite composition;
  particulate $RuO_2$ in an amount of at least 5% by weight (determined as Ta) of the composite composition; and
  particulate graphite in an amount of at least 5% by weight of the composition; and optionally
  up to 5% by weight of other metal oxides selected from the group consisting of $PtO_2$, $IrO_2$, $TiO_2$, $Er_2O_3$, $ZrO_2$, $Si_3N_4$, $Al_2O_3$ and mixtures thereof.

In a further set of embodiments there is provided a method of preparing a pH sensor comprising a metal oxide-polymer composite, the method comprising dispersing a solid particulate component comprising metal oxides and carbon-based conductor in a hardenable liquid resin and causing the liquid resin to harden wherein the metal oxides comprises $Ta_2O_5$ and $RuO_2$ in a weight ration of $Ta_2O_5:RuO_2$ in the range of from 90:10 to 10:90, preferably from 80:20 to 20:80 and more preferably from 70:30 to 30:70.

In a further set of embodiments there is provided a pH sensor comprising a metal oxide-polymer composite as hereinbefore described and a metallic conductor in electrical communication with the metal oxide-polymer composite.

BRIEF DESCRIPTION OF DRAWINGS

Embodiments of the invention are described with reference to the attached drawings. In the drawings.

DETAILED DESCRIPTION

Figure 1:
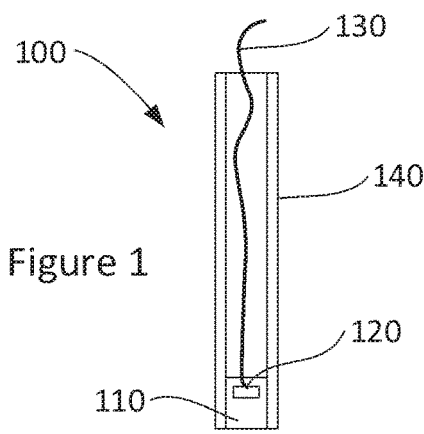
FIG. 1 is a schematic cross section of a mixed metal oxide-polymer composite mounted on a wire and disposed within a ceramic tube to form a working pH sensor in accordance with an embodiment of the invention.

The pH sensor comprises a metal oxide-polymer composite. The metal oxide-polymer composite comprises $RuO_2$ and $Ta_2O_5$, and optionally also other metal oxides with a particulate carbon-based conductor dispersed in a polymer matrix. We have found that the pH sensing characteristics of the composite provide fast response times, are not sensitive to common cations and allow the use of economical fabrication methods. The composite also allows formation of miniature pH sensors and their use in a wide range of environments including industrial minerals processing, food processing, environmental monitoring and in biological systems.

The metal oxide component of the metal oxide-polymer composite includes $RuO_2$ and $Ta_2O_5$ in a weight ratio of $Ta_2O_5$:$RuO_2$ (based on metal component in the oxides) in the range of from 90:10 to 10:90, preferably from 80:20 to 20:80 and more preferably from 70:30 to 30:70. This presence of the $RuO_2$ and $Ta_2O_5$ metal oxide particularly in these ratios provides an improvement in the sensitivity and resistance to interfering ion species which was not expected from the contribution of the respective metal oxides.

The metal oxide component of the metal oxide-polymer composite may include other metal oxides however in one set of embodiments it is generally preferred that the total of the $RuO_2$ and $Ta_2O_5$ content constitute at least 70% by weight, preferably at least 80% by weight and most preferably at least 90% by weight of the total metal oxide content of the composite.

The metal oxide component of the composite may thus comprise further metal compounds such as one or more selected from the group consisting of $PtO_2$, $IrO_2$, $TiO_2$, $Er_2O_3$, $ZrO_2$, $Si_3N_4$, $Al_2O_3$, $RhO_2$, $SnO_2$, $La_2O_3$ and $Li_2O$.

The total amount of the metal oxides in addition to $RuO_2$ and $Ta_2O_5$ is preferably in an amount of no more than 20% by weight, preferably from 5% to 20% of the total metal oxide component including $RuO_2$ and $Ta_2O_5$.

The amount of $Ta_2O_5$ based on the total composite weight will depend on the sensitivity required, the ratio of $RuO_2$:$Ta_2O_5$ and nature and amount of other components such as the polymer and carbon based conductor. The particle size of the metal oxides may also have a bearing on the amount used. In one set of embodiments the amount of $Ta_2O_5$ (determined as Ta metal component) is at least 1% by weight of the composite composition, preferably at least 5% by weight. In certain embodiments the $Ta_2O_5$ content (based on Ta metal component) is in the range of from 1% to 25% by weight of the composite composition and more preferably in the range of from 5% to 25% such as 5% to 20% or 5% to 15% by weight of the composite composition.

The amount of $RuO_2$ based on the total composite weight will depend on the sensitivity required, the ratio of $RuO_2$:$Ta_2O_5$ and nature and amount of other components such as the polymer, carbon based conductor and any other metal oxides. The particle size of the metal oxides may also have a bearing on the amount used. In one set of embodiments the amount of $RuO_2$ (determined as Ru metal component) is at least 1% by weight of the composite composition, preferably at least 5% by weight. In certain embodiments the $RuO_2$ content (based on Ru metal component) is in the range of from 1% to 25% by weight of the composite composition and more preferably in the range of from 5% to 25% such as 5% to 20% or 5% to 15% by weight of the composite.

The particle size of the metal oxide has a bearing on the sensitivity and performance of the composite in monitoring pH. The optimum particle size may depend on the carbon-conductor content and the concentration of the components. In one set of embodiments the average particle size is less than 100 microns. We have found that particularly good results are generally achieved where the average particle size is less than 10 microns and particularly less than 5 microns. The value of using particles of particularly small size may be reduced by the cost of obtaining such particles. In one set of embodiments the particles are more than 20 nanometers, such as more than 50 nanometers or more than 100 nanometers in average size.

The solid particulate component dispersed in the polymer resin matrix comprises a carbon based conductor.

In one set of embodiments, the particulate component comprising the metal oxides and particulate carbon-based conductor constitute at least 40% by weight of the composite composition, preferably from 60% to 80% by weight of the composite composition.

The particulate carbon based conductor may be selected from a wide range of known carbon based conductors. Carbon based conductors may, for example, be selected from particulate carbon, graphite, fullerenes and carbon fibre.

The carbon based conductor may have a range of different morphologies depending on the nature and chemical structure of the carbon based conductor. The particulate carbon based conductor may comprise spherical particles, platelets, rods, fibres or combinations thereof and hence the particles may have non-uniform dimensions. In one set of embodiments the particle size is less than 100 microns such as less than 10 microns or less than 5 microns. In another embodiment the particles are elongated and of up to 1 mm in length such as up to 500 mm. The carbon-based conductor particles may, in the case of fibres, have a range of aspect ratios (maximum/minimum dimensions) such as aspect ratio of 1.5:1 to 20:1.

The more preferred carbon based conductor is selected from the group consisting of particulate carbon and particulate graphite.

In one set of embodiment the carbon based conductor comprises in the range of from 10% to 70% by weight of the composite composition and preferable in the range of from 15% to 80% by weight of the composite composition.

The particulate component including the metal oxides and carbon based conductor are dispersed in a polymer resin matrix.

The polymer matrix may be selected from a wide range of suitable resins. The resin will generally be resistant to a range of pH conditions. Suitable polymer resins may be selected from the group consisting of, polystyrene, polyurethane, polyolefins (such as polyethylene, polypropylene and polyolefin blends), acrylates, methacrylates, vinyl resins, vinyl ester resin, phenol resin, epoxy resin and mixtures thereof.

In one set of preferred embodiments the pH sensor comprises a metal oxide-polymer composite which comprises:
 a polymer matrix in an amount of at least 15% by weight of the composite composition and dispersed in the matrix a mixture of particulate materials comprising:
  (i) particulate $Ta_2O_5$ in an amount of at least 5% by weight (determined as Ta) of the composite composition;
  (ii) particulate $RuO_2$ in an amount of at least 5% by weight (determined as Ta) of the composite composition; and
  (iii) particulate graphite in an amount of at least 5% by weight of the composition; and optionally
  (iv) up to 5% by weight of other metal oxides selected from the group consisting of $PtO_2$, $IrO_2$, $TiO_2$, $Er_2O_3$, $ZrO_2$, $Si_3N_4$, $Al_2O_3$ and mixtures thereof.

In a preferred set of embodiments the composite comprises:
 a polymer matrix in an amount of from 15% to 80% (more preferably 20% to 50%) by weight of the composite composition and dispersed in the matrix a mixture of particulate materials comprising:
  (i) $Ta_2O_5$ in an amount (based on Ta metal component) of from 5% to 25% such as 5% to 20% or 5% to 15% by weight of the composite;
  (ii) $RuO_2$ an amount (based on Ru metal component) in the range of from 5% to 25% such as 5% to 20% or 5% to 15% by weight of the composite;
  (iii) carbon based conductor in an amount in the range of from 10% to 70% by weight of the composite composition and preferable in the range of from 15% to 60% by weight of the composite composition; and
  (iv) 0% to 5% by weight of other metal oxides selected from the group consisting of PtO2, IrO2, TiO2, Er2O3, ZrO2, Si3N4, Al2O3 and mixtures thereof.

In a further set of embodiments there is provided a pH sensor comprising the composite as hereinbefore described provided on a conductive substrate for connection to a circuit for measuring potential change attributable to pH change. The conductive substrate may be a metal wire, rod, fibre, strip sheet or the like and the composite of the invention lends itself to being used in a range of applications and structures. The circuit may include a reference electrode of well known type.

One of the advantages of the composite for use as a pH sensor is that it may be formed in a wide range of shapes and forms to provide pH sensors designed for specific applications.

The metal oxide-polymer composite may be formed using a liquid resin which allows the particulate materials to be dispersed in the liquid resin and the liquid resin transformed to a hardened state. This allows the composite to be incorporated into a moulded structure, applied as a coating to a suitable substrate or printed onto a suitable substrate. Suitable substrates may be conductive such as metals which may form part of a signal processing circuit. Alternatively, the substrate may simply provide a support for the composite and be conducting or non-conducting with a separate conducting connection being provided to the composite for signal processing.

In one embodiment the polymer resin is a thermoplastic and the particulate materials are incorporated into the resin matrix while the resin is in a thermally induced plastic state. For example the polymer resin of thermoplastic type may be plasticized and blended in the plasticized state with the particulate materials, In a further example a thermoplastic polymer in particulate form may be mixed with the particulate metal oxide and carbon based conductor and moulded with application of heat to fuse the resin with the particulate metal oxide and carbon based conductor dispersed therein. The resins prepared by thermal processing can include, but not be limited to, such resin materials as polyethylene, polypropylene, polyvinyl chloride, polystyrene, polyurethane, polyethers and polyvinylidene fluoride.

In another set of embodiments the polymer resin and particulate material is dispersed in a suitable liquid medium and a solid composite is produced by co-deposition or removal of the solvent. For example PVC may be dispersed in a solvent, such as DMF, allowing co-dispersion of the particulate materials and the composite produced by separation of the composite from the solvent (for example by addition of water where the solvent is DMF).

In another embodiment the liquid resin is a liquid polymerizable composition which can be hardened by polymerization to form the polymer resin. The precursor may comprise one or more monomers or prepolymers in which the particulate materials are dispersed prior to curing to form the polymer resin matrix. Curing may be carried out by a wide range of polymerization processes known in the art for forming different polymers such as thermosets, polymerisation catalysts, UV curable compositions and the like. The hardenable resin can be a phenol-formaldehyde resin, a phenol-furfural resin may for example be bisphenol epoxy resin, a halogenated bisphenol epoxy resin, a peracteic acid oxidized polyolefin epoxy resin, a methyacrylate resin, an acrylate resin, epoxy resin or any combination thereof.

In one embodiment the polymer resin is formed from a hardenable liquid resin and a hardening catalyst, these components preferably being stored separately until the resin is required to set hard. When the components are mixed the resin hardens by a process of cross-linking and/or polymerisation. The liquid resin and hardening catalyst may be mixed together before mixing with the particulate material or mixing with the liquid resin and particulates to be carried out prior to addition of the hardening catalyst. The appropriate order of mixing may depend on the speed of hardening with the chosen components and reaction conditions. One preferred example is a liquid epoxy resin and amine based hardening catalyst.

The pH sensor may comprise the composite formed about a substrate or as a coating or printed structure on a substrate. In one set of embodiments the resin is applied in liquid form to a substrate such as a wire, rod, fiber, sheet or the like and hardened. The liquid resin may be applied to a surface by coating or by printing and hardened to form the polymer resin matrix.

We have found that pH sensors of mixed $Ta_2O_5$ and $RuO_2$ metal oxides with graphite powders and polymer resin to form metal oxide composites show linear Nernstian response between pH 1-12 with the slope of 40-60 mV/pH unit.

The pH sensor shows robust resistance to acid, high temperature and pressure making it suitable for use in a wide range of applications in the food processing, industrial chemistry, research and minerals processing in which conventional pH electrodes are not able to operate. The sensor may also be produced at a relatively low cost compared with conventional electrodes. A significant advantage of the pH sensor is in the ability to vary the dimensions, shape and supporting substrate used in fabrication of the pH sensor. The composite may be moulded to a variety of shapes or can be applied by a wide range of coating and printing techniques making the technology much more amenable to different uses and applications.

There is also a very significant improvement from reduced interference in the pH sensor compared with similar metal oxide based pH sensors. Indeed, the presence of both ruthenium and tantalum oxides in the required ratio significantly reduces interference from ions commonly present in environments where pH monitoring is required.

Examples of pH sensors will be described with reference to the attached drawings.

FIG. 1 shows a simple pH working sensor (100) in accordance with an embodiment of the invention which comprises a pH sensing composite in accordance with the invention (110) which is connected at a connection point (120) to a wire (130) for connection to a circuit for measuring potential change attributable to pH change. The pH sensor may further comprise a protector (140) for protecting the composite and connection (120). The protector (140) may be formed of a suitable plastics material.

Figure 2:
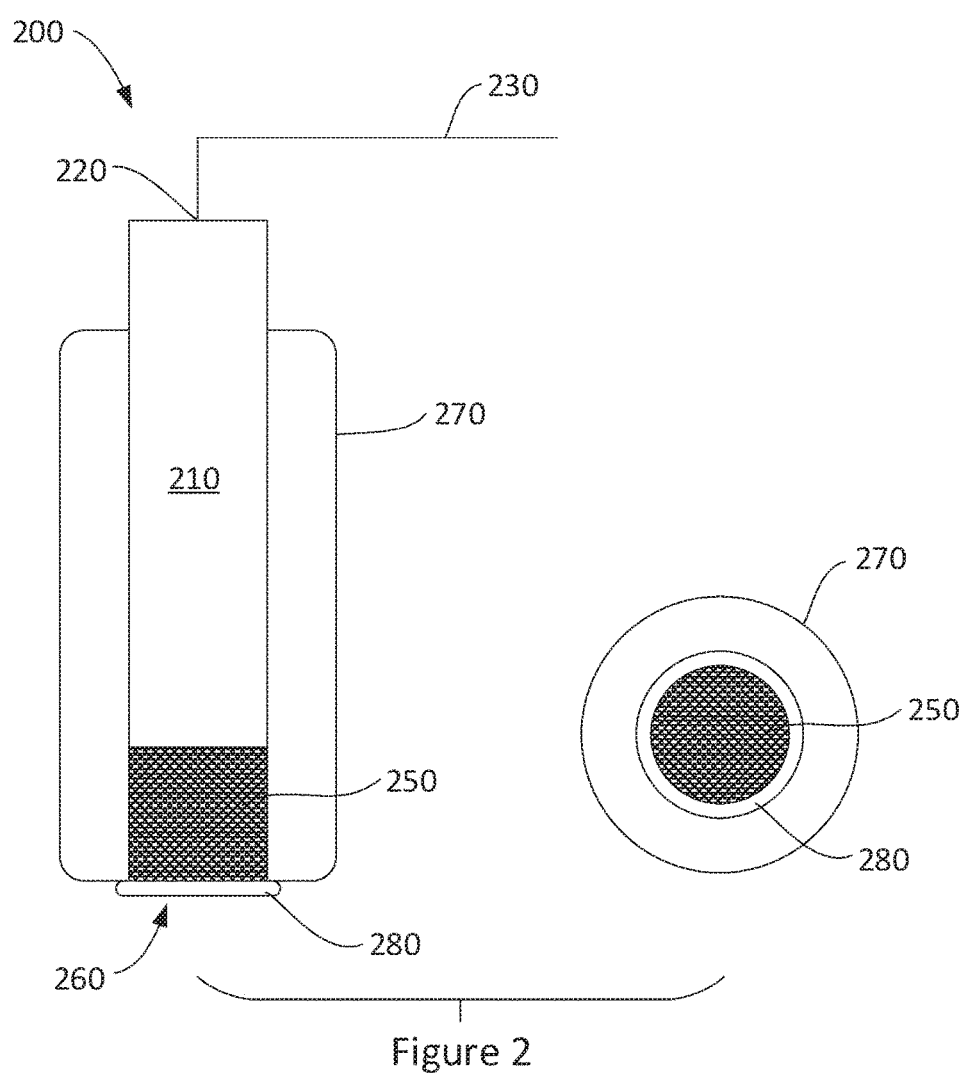
FIG. 2 is a schematic cross section of a pH sensor comprising a mixed metal oxide-polymer composite in accordance with an embodiment of the invention.

FIG. 2 shows a pH sensor (200) in accordance with a further embodiment of the invention which is adapted for use in the corrosive environment such as an acid leach mineral recovery process. An electrode portion (210) is connected at connection point (220) to a wire (230) for connection to a circuit for measuring potential change attributable to pH change. The electrode (210) is formed of an elongate conductive metal substrate such as a metal rod or strip and which has a coating of pH sensing composite (250) in accordance with the invention at the operational end (260) remote from connection point (220). The pH sensor (300) is provided with a protector (270) in the form of a plastic shell extending about the composite coated portion (250) of the sensor and comprises a membrane (280) at the operational end (280) allowing ingress of liquid subject for pH determination for contact with the composite (250).

Figure 3:
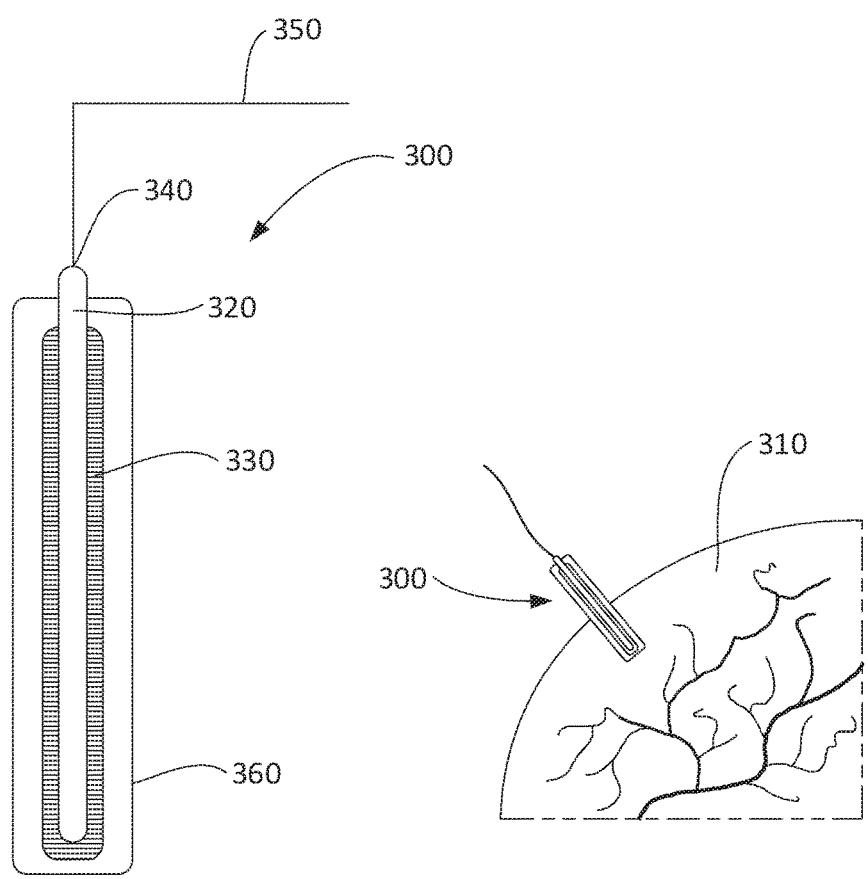
FIG. 3a is a schematic cross section of an pH sensor comprising a mixed metal oxide-polymer composite coating a conductive needle or fibre. The sensor of FIG. 3a may be used as a pH sensor of a biological sample.
FIG. 3b is a schematic representation of the pH sensor as an implant in a biological sample.

FIGS. 3a and 3b show a pH sensor (300) for use in determining the pH of a biological material (310) in which it may be implanted as shown in FIG. 3b. The pH sensor has an electrode portion comprising a conductive needle or fiber (320) provided with a coating of pH sensing composite (330) in accordance with the invention. The electrode conductive portion (320) is connected at connection point (340) to a wire (350) for connection to a circuit for measuring potential change attributable to pH change. The operative portion of the electrode may be protected by a membrane (360) which allows the ingress of liquid subject to pH determination from the biological material (310). The pH sensor of this embodiment may be fabricated in a very small size such as 100 microns to 1 mm in size and in a range of shapes.

The invention will now be described with reference to the following examples. It is to be understood that the examples are provided by way of illustration of the invention and that they are in no way limiting to the scope of the invention.

EXAMPLES

Examples 1 to 3 and Comparative Examples 4 and 5

Composites and electrodes of these examples were prepared using the general method described below to prepare electrode with composited shown in Table 1.

Preparing a Mixed Metal Oxide-Polymer Composite Electrode:

1. Epoxy Polymer resin (bisphenol-A-epichlorhydrin) is mixed with curing agent (3-aminomethyl-3,5,5-trimethylcyclohexylamine) just before the preparation of the electrode.
2. Metal oxide powders (particle size<5 µm), graphite (particle size<20 µm) and polymer are weighed.
3. Metal oxide powders and graphite are mixed together (and possibly grinded) for 2-5 minutes to prepare a homogeneous powder. Additional metal oxides such as lanthanum (III) oxide, lithium oxide and mixtures thereof may be used in a total amount of up to 5% by weight if desired.
4. Polymer is mixed thoroughly with graphite-metal oxide powder in a jar (low consistency) or with mortar and pestle (high consistency) for 2-5 minutes.
5. Paste or suspension is formed into the shape of an electrode for example by:
   a. Pressing the paste inside a plastic tube (FIG. 1)
   b. Printing the composite on a conductive substrate (FIG. 2)
   c. Dip-coating composite on a conductive fiber (FIG. 3)
6. Mixed metal oxide-polymer composite is cured in oven at 60° C. for 2-4 hours and possibly polished with 1200 grit sandpaper.
7. In order to prevent the interference of some ions and redox-active species on sensor signal, protective membrane (nafion, polyurethane etc.) can be coated on top of the sensing material.
8. Sensor and reference electrode, e.g. Ag/AgCl (3 M KCl), are connected into a potential logging device.
9. Sensor is calibrated by recording potential values of the sensor in pH buffer solutions, e.g. pH 4, pH 7 and pH 10.

TABLE 1

Examples of the composition of the mixed metal oxide sensors and single metal oxide sensors.

| Example | Polymer | Graphite | Ta2O5 | RuO$_2$ *3H$_2$O |
|---|---|---|---|---|
| 1 | 40.4 | 17.9 | 10.5 | 31.2 |
| 2 | 39.9 | 30.1 | 15.0 | 15.1 |
| 3 | 30.1 | 35.1 | 8.6 | 26.2 |
| CE4 | 40.8 | 29.7 | 0.0 | 29.5 |
| CE5 | 40.0 | 30.1 | 29.9 | 0.0 |

Sensitivity of the mixed metal oxide electrodes to protons (pH) was higher than pure metal oxide composite electrodes of Comparative Examples 4 and 5 (CE4 and CE5).

Hysteresis of the slope was smaller for the mixed metal oxide electrodes compared to the pure metal oxide electrodes (difference between acid to base and base to acid slopes), Intercept (mV at pH 0) point was more stable for the mixed metal oxide sensors.

TABLE 2

Slope and intercept of the composite electrode and difference of sensor signal measured from acidic pH towards basic pH and vica versa.

| Example | Slope (mV/pH unit) | | | Intercept (mV) | | |
|---|---|---|---|---|---|---|
| | Acid to base | Base to acid | Diff. | Acid to base | Base to acid | Diff. |
| Day 1 | | | | | | |
| 1 | −58.6 | −57.3 | −1.3 | 694.9 | 678.4 | 16.5 |
| 2 | −57.6 | −58.0 | 0.4 | 657.2 | 661.7 | −4.5 |
| 3 | −58.9 | −58.2 | −0.7 | 697.9 | 685.6 | 12.3 |
| CE4 | −54.1 | −51.7 | −2.4 | 672.4 | 641.7 | 30.7 |
| CE5 | −45.6 | −28.8 | −16.8 | 412.9 | 274.9 | 138.0 |
| Day 7 | | | | | | |
| 1 | −55.5 | −56.1 | 0.6 | 607.5 | 604.4 | 3.1 |
| 2 | −56.6 | −56.5 | −0.1 | 592.5 | 584.1 | 8.4 |
| 3 | −57.5 | −57.6 | 0.1 | 609.3 | 605.2 | 4.1 |
| CE4 | −44.5 | −45.4 | 0.9 | 532.7 | 519.8 | 12.9 |
| CE5 | −42.2 | −29.3 | −12.9 | 370.2 | 261.8 | 108.4 |

Figure 4:
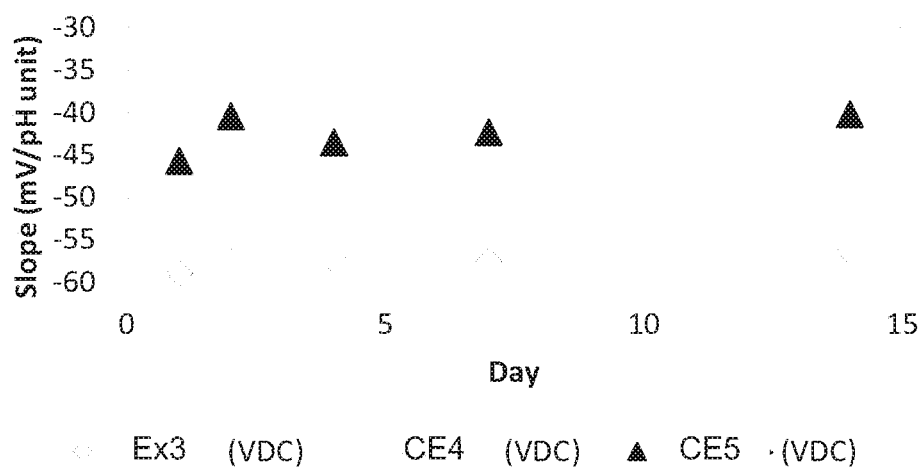
FIG. 4 is a graph comparing the slope of the mixed metal oxide composite pH sensor of an embodiment of single metal oxide sensors not of the invention referred to in the Example 5.

FIG. 4 shows a plot of the slope of the ph sensors of Example (ex) 3 and Comparative Examples (CE) 4 and 5.

Slope of the mixed metal oxide sensor stabilised during the first 2 days (stored in pH 7 buffer). Mixed metal oxide sensor maintained high sensitivity to protons for several weeks whereas pure metal oxide sensors suffered significant loss of sensitivity (−10 mV/pH or more).

Intercept point of the calibration slope stabilised during the first 2 days of storage (pH 7 buffer).

Figure 5:
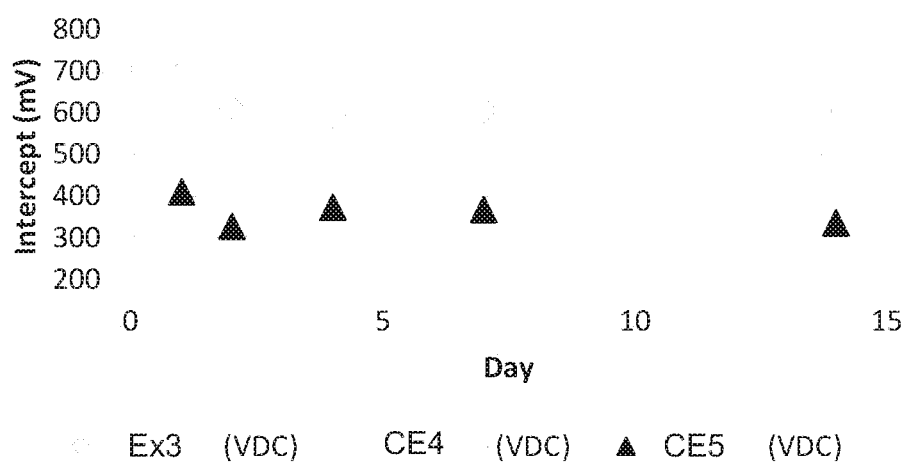
FIG. 5 is a graph showing the Intercept point of the calibration of the mixed metal oxide composite pH sensor of an embodiment and single metal oxide pH sensors not of the invention as referred to in the Examples.

FIG. 5 shows the intercept point of the calibration of the mixed metal oxide composite sensor (Ex 3) and single metal oxide sensors (CE4 and CE5).

Mixed metal oxide sensors were less sensitive to chlorides than pure metal oxide sensors.

TABLE 3

Interference caused by the Cl⁻ anions and difference of the measured pH between a commercial and mixed metal oxide composite electrode.

| Example | 1 | CE4 | CE5 |
|---|---|---|---|
| | Measured pH | | |
| Cl⁻ 0.03M | 6.957924 | 6.943846 | 6.996631 |
| Cl⁻ 0.3M | 6.778634 | 6.707098 | 6.745546 |
| Cl⁻ 0.6M | 6.697703 | 6.594617 | 6.482754 |
| | Difference between sensors | | |
| Cl⁻ 0.03M | −0.00308 | −0.01715 | 0.035631 |
| Cl⁻ 0.3M | −0.01037 | −0.0819 | −0.04345 |
| Cl⁻ 0.6M | −0.0133 | −0.11638 | −0.22825 |

The invention claimed is:

1. A pH sensor comprising a metal oxide-polymer composite, comprising:
   a continuous polymer resin matrix; and
   a solid particulate component dispersed in the polymer resin matrix comprising (i) particulate metal oxides and (ii) a particulate carbon-based conductor,
   wherein the particulate metal oxides comprise $Ta_2O_5$ and $RuO_2$ in a weight ratio based on Ta:Ru in the range of from 90:10 to 10:90.

2. A pH sensor according to claim 1 wherein the composite comprises a weight ratio $Ta_2O_5$:$RuO_2$ in a weight ratio based on Ta:Ru in the range of from 70:30 to 30:70.

3. A pH sensor according to claim 1, wherein the solid particulate component comprising the particulate metal oxides and the particulate carbon-based conductor constitutes at least 40% by weight of the composite composition.

4. A pH sensor according to claim 1, wherein the solid particulate component comprises in the range of from 60% to 80% by weight of the composite.

5. A pH sensor according to claim 1, wherein the particulate carbon-based conductor comprises a material selected from the group consisting of particulate carbon, graphite, fullerenes and carbon fibre.

6. A pH sensor according to claim 1, wherein $Ta_2O_5$ and $RuO_2$ constitute at least 80% by weight of a total metal oxide content of the composite.

7. A pH sensor according to claim 1, wherein the particulate metal oxides comprise, in addition to $Ta_2O_5$ and $RuO_2$, further metal oxides, the further metal oxides comprising up to 20% by weight of a total metal oxide component of the metal oxide-polymer composite.

8. A pH sensor according to claim 7, wherein the further metal oxides comprise one or more metal compounds selected from the group consisting of $PtO_2$, $IrO_2$, $TiO_2$, $Er_2O_3$, $ZrO_2$, $Al_2O_3$, $RhO_2$, $SnO_2$, $La_2O_3$ and $Li_2O$.

9. A pH sensor according to claim 1, wherein the particulate carbon-based conductor is selected from the group consisting of particulate carbon and particulate graphite.

10. A pH sensor according to claim 1, wherein the particulate metal oxides are of particle size less than 100 microns.

11. A pH sensor according to claim 1, wherein the polymer matrix comprises a resin selected from the group consisting of; polystyrene, polyurethane, polyethylene, acrylates, methacrylates, vinyl resins, vinyl ester resin, phenol resin, epoxy resin and mixtures thereof.

12. A pH sensor according to claim 1, wherein the metal oxide-polymer composite comprises:
   the resin polymer matrix in an amount of at least 15% by weight of the composite, wherein the solid particulate component dispersed in the matrix comprises:
   (i) particulate $Ta_2O_5$ in an amount of at least 5% by weight, determined as Ta, of the composite;
   (ii) particulate $RuO_2$ in an amount of at least 5% by weight, determined as Ru, of the composite; and
   (iii) particulate graphite in an amount of at least 5% by weight of the composite; and optionally
   (iv) up to 5% by weight of the composite of other metal oxides selected from the group consisting of $PtO_2$, $IrO_2$, $TiO_2$, $Er_2O_3$, $ZrO_2$, $Si_3N_4$, $Al_2O_3$ and mixtures thereof.

13. A method of preparing the pH sensor according to claim 1, the method comprising dispersing the solid particulate component comprising the metal oxides and the carbon-based conductor in a hardenable liquid resin and hardening the liquid resin to form the polymer resin matrix with the dispersed solid particulate component dispersed therein, wherein the metal oxides comprise $Ta_2O_5$ and $RuO_2$ in a weight ratio based on Ta:Ru in the range of from 90:10 to 10:90.

14. A method of preparing a pH sensor according to claim 13, wherein the polymer resin matrix comprises an epoxy resin.

15. A pH sensor according to claim 1, further comprising a substrate to which the metal oxide-polymer composite has been applied.

16. A method of preparing a pH sensor according to claim 13, wherein the hardenable liquid resin comprising the dispersed solid particulate component is applied to a substrate by printing and is hardened on the substrate.

17. A pH sensor according to claim 1, wherein the composite has a particulate $Ta_2O_5$ content, determined as Ta metal component, of 5% to 25% by weight of the composite.

18. A pH sensor according to claim 1, wherein the composite has a particulate $RuO_2$ content, determined as Ru metal component, of 5% to 25% by weight of the composite.

* * * * *